(12) United States Patent
Buchhauser et al.

(10) Patent No.: US 8,968,672 B2
(45) Date of Patent: *Mar. 3, 2015

(54) APPARATUS FOR DISINFECTING CONTAINER CLOSURES

(71) Applicant: Krones AG, Neutraubling (DE)

(72) Inventors: Klaus Buchhauser, Deuerling (DE); Guenter Frankenberger, Koefering (DE); Sebastian Klepatz, Regensburg (DE)

(73) Assignee: Krones AG, Neutraubling (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,803

(22) Filed: Apr. 30, 2013

(65) Prior Publication Data

US 2013/0243648 A1   Sep. 19, 2013

Related U.S. Application Data

(63) Continuation of application No. 12/233,685, filed on Sep. 19, 2008, now Pat. No. 8,449,819.

(30) Foreign Application Priority Data

Sep. 20, 2007   (DE) .......................... 10 2007 045 142

(51) Int. Cl.
*A61L 2/00* (2006.01)
*B65B 55/04* (2006.01)
(Continued)

(52) U.S. Cl.
CPC . *A61L 2/20* (2013.01); *A61L 2/208* (2013.01); *B08B 7/00* (2013.01); *B67B 3/003* (2013.01); *A61L 2202/17* (2013.01)
USPC ........................................... 422/292; 53/426

(58) Field of Classification Search
CPC .................................. B67B 3/003; A61L 2/20
USPC ............................................. 422/292; 53/426
See application file for complete search history.

(56) References Cited

U.S. PATENT DOCUMENTS 3,744,209 A * 7/1973 Conley et al. ................... 53/426
5,209,902 A   5/1993 Matthews et al.
(Continued)

FOREIGN PATENT DOCUMENTS

DE          29708145        12/1997
DE          10145102        4/2003
(Continued)

OTHER PUBLICATIONS

English Translation of Japanese Document No. JP 11342917 A provided by the Industrial Property Digital Library: Yamaguchi et al., Cap Treatment Device and Cap Sterilization Device Using the Cap Treatment Device, Dec. 14, 1999.

(Continued)

*Primary Examiner* — Kevin Joyner
(74) *Attorney, Agent, or Firm* — Onello & Mello, LLP

(57) ABSTRACT

The invention relates to an apparatus for disinfecting container closures, comprising a housing and comprising a transport path which is arranged inside the housing and along which the closures are transported, wherein the transport path has at least partially a spiral configuration. According to the invention, the apparatus comprises a supply device for supplying to the housing a gaseous medium for disinfecting the container closures, and at least one displacement device is provided which can move with respect to the housing and which transports the container closures along the spiral transport path.

20 Claims, 3 Drawing Sheets

(51) Int. Cl.
  *A61L 2/20* (2006.01)
  *B08B 7/00* (2006.01)
  *B67B 3/00* (2006.01)

(56) References Cited

U.S. PATENT DOCUMENTS

| | | | |
|---|---|---|---|
| 7,536,839 B2 | 5/2009 | Kemper et al. | |
| 2002/0029543 A1* | 3/2002 | Taggart | 53/426 |
| 2005/0247028 A1 | 11/2005 | Topf | |
| 2007/0006550 A1 | 1/2007 | Kemper et al. | |

FOREIGN PATENT DOCUMENTS

| | | |
|---|---|---|
| DE | 69903355 | 6/2003 |
| EP | 0329632 | 8/1989 |
| JP | 11342917 | 12/1999 |
| WO | 2007147535 | 12/2007 |

OTHER PUBLICATIONS

Chinese Search Report issued on May 21, 2012 in corresponding Chinese Patent Application 200810211250.4.

Definition for "spiral" provided by dictionary.reference.com: spiral. (n.d.). Dictionary.com Unabridged. Retrieved Jun. 10, 2011, from Dictionary.com website: http://dictionary.reference.com/browse/spiral.

Definition for "helix" provided by dictionary.reference.com: helix. (n.d.). Dictionary.com Unabridged. Retrieved Jun. 10, 2011, from Dictionary.com website: http://dictionary.reference.com/browse/helix.

International Search Report dated Feb. 9, 2009 issued in corresponding International Application No. EP08164555.

* cited by examiner

APPARATUS FOR DISINFECTING CONTAINER CLOSURES

RELATED APPLICATIONS

This application claims benefit to U.S. Ser. No. 12/233,685 now U.S. Pat. No. 8,449,819 filed on Sep. 19, 2008 which relies for priority upon German Patent Application No. 10 1007 045 142.5, filed on Sep. 20, 2007, the contents of which are herein incorporated by reference in their entirety.

DESCRIPTION

The present invention relates to an apparatus for disinfecting closures and in particular container closures. In beverage production, it is customary to sterilise and to clean not only the containers themselves prior to filling but also the closures for the containers. Such cleaning may take place for example via a cleaning liquid, with the closures being guided into an appropriate liquid bath.

An apparatus for cleaning and/or sterilising closure caps is known from DE 297 08 145 U1. In said document, the closure caps are transported through a channel and in the process are acted upon by liquid. This channel is designed in the form of a substantially horizontal spiral which extends through an immersion bath.

In many sectors, however, it is desirable to carry out the cleaning of these closures in a dry process, i.e. to omit such an immersion bath. The object of the present invention is therefore to provide an apparatus for cleaning container closures which allows dry cleaning or cleaning without using a liquid cleaning agent. This is achieved according to the invention by the subject matters of independent claims 1, 12 and 15. Advantageous embodiments and further developments form the subject matter of the dependent claims.

An apparatus according to the invention for disinfecting container closures comprises a housing and also a transport path or transport channel which is arranged inside this housing and along which the closures are transported. Here, this transport path has at least partially a spiral configuration. According to the invention, the apparatus comprises a supply device for supplying to the housing a gaseous medium for disinfecting the closures, and a displacement device is provided which can move with respect to this housing and which transports the closures along the spiral transport path. Preferably, the housing is designed in a gas-tight manner, at least in the region in which the transport path runs.

In a further advantageous embodiment, the housing has a housing wall which surrounds the transport path and in which a large number of supply devices in the form of nozzles are arranged.

In a further advantageous embodiment, the displacement device comprises a large number of displacement bodies which are arranged such that they can rotate around a common axis. By means of these displacement bodies, the individual container closures are guided along the aforementioned transport path.

In a further advantageous embodiment, the transport path is designed in such a way that the closures are transported along the spiral from the outside towards the inside. In such an embodiment, an inlet star wheel may with particular advantage be arranged at the outer circumference of the spiral, which inlet star wheel feeds the individual closures to the spiral path.

In a further advantageous embodiment, the displacement bodies are arranged on a common support. Advantageously, the displacement bodies have an outer section which is curved in the movement direction, and particularly preferably also a region which is inclined with respect to the radial direction of the displacement bodies. In this way, the individual container closures are urged slightly radially inwards during the displacement movement, so that it is possible to prevent any jamming of the container closures within the transport path.

Preferably, the displacement bodies are arranged on a common support. This common support is in turn arranged such that it can rotate with respect to a rotation axis, which particularly preferably runs substantially in the centre of the spiral transport path.

This means that all the displacement bodies move at the same speed of rotation with respect to the housing. It is possible here for the transport path to be delimited by the displacement bodies in such a way that in each case one container closure is guided between two displacement bodies. However, it would also be possible for a plurality of container closures to be guided by one displacement body.

In a further advantageous embodiment, the apparatus comprises a support device along which the closures are displaced, and the transport path is formed by this support device and a spirally curved guide device. Preferably, the support device is a base on which the closures rest and along which they are moved. The spirally curved guide device is preferably a wall which extends perpendicular to this base and which runs in a spiral manner in order to be able to guide the container closures along this Preferably, the guide device is arranged at a distance from the support device in a direction perpendicular to the support device, and with particular preference this distance lies in a range of 4-6 mm.

Preferably, the housing also has an inlet region, via which the container closures are fed in, and an outlet region, via which the container closures are discharged. Preferably, an aspirating device for the gaseous medium is provided at least in the outlet region or in the inlet region. With particular preference, an aspirating device for the gaseous medium is arranged both in the outlet region and in the inlet region.

In a further advantageous embodiment, the displacement bodies are arranged in such a way that they contact the closures on a base body thereof. Conversely, therefore, the closure bodies are not contacted on their tops. In this way, the apparatus is suitable also for container closures of different heights.

In a further advantageous embodiment, the transport path is adjoined by a transport chute with preferably an S-shaped profile. Via this transport chute, the container closures are conveyed out of the apparatus.

In a further advantageous embodiment, a pivotable cover is arranged on the housing and above the housing. This cover can be opened in order to give the user access to the individual container closures.

In a further advantageous embodiment, a large number of cleaning nozzles for cleaning the housing are arranged inside the housing. These may be cleaning nozzles which allow internal cleaning of the housing outside normal operation, for example even with liquids. Preferably, a heating device for the gaseous medium is provided on the housing. In this case, the container closures are preferably transported through the housing in which gaseous hydrogen peroxide at temperatures of between 40° and 50° C. acts on the container closures for approx. 20-30 seconds. As mentioned above, the outlet of this housing is already located in a cleanroom. The heating device causes the gaseous medium, i.e. in particular the hydrogen peroxide, to be heated before entering the housing.

The present invention also relates to an arrangement for disinfecting container closures, comprising an apparatus of the type described above and also a feed device which feeds the closures to the transport path. According to the invention, the feed device comprises a transport wheel which feeds the closures individually to the transport path. As a result, the closures are delivered to the displacement device or to the individual displacement bodies in a precisely defined manner.

Preferably, the transport wheel is accommodated in the housing of the apparatus.

In further advantageous embodiments, the gaseous medium is at least temporarily at a higher pressure in the region of the housing in which the transport path is provided than in the region of the housing in which the transport wheel is arranged. A pressure drop thus takes place from the region of the transport path towards the region of the transport wheel, as a result of which the gaseous medium can be discharged from the housing in a defined manner.

The present invention also relates to a method for cleaning container closures, wherein the containers during the cleaning operation are guided along a transport path arranged inside a housing, and wherein the transport path has at least partially a spiral configuration. According to the invention, a gaseous medium is supplied to the container closures for sterilisation purposes during transport on the transport path inside the housing.

Further advantages and embodiments will emerge from the appended drawings:

Figure 1:
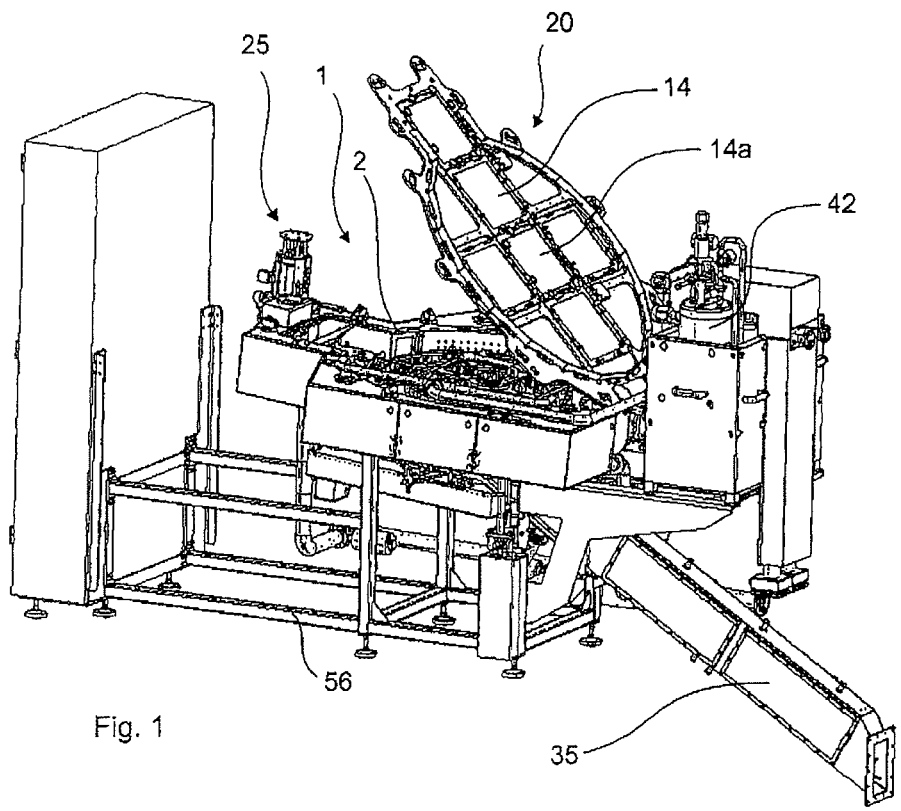
FIG. 1 shows an overall view of an arrangement according to the invention for disinfecting container closures.

FIG. 1 shows an arrangement 20 according to the invention for disinfecting container closures. This arrangement 20 comprises a frame 56 on which there is arranged a housing 2 for the apparatus 1 for disinfecting container closures. Reference 14 denotes a cover, by means of which the housing can be covered or closed in a gas-tight manner. This cover 14 is arranged pivotably on the housing 2 and has viewing windows 14a. It is preferably also possible that individual viewing windows 14a can be opened separately. The opening and closing of the cover 14 takes place pneumatically. Opening by means of a cable winch is also conceivable.

A gaseous medium, such as hydrogen peroxide for example, is supplied to the housing 2 from a reservoir 42. The container closures can be fed to the housing 2 via a feed device 25. Inside the housing 2, the container closures are transported along a transport path (discussed in more detail below) and specifically from the outside towards the inside in the embodiment shown in the figures, and finally pass out of the arrangement via a discharge channel 35.

Figure 2:
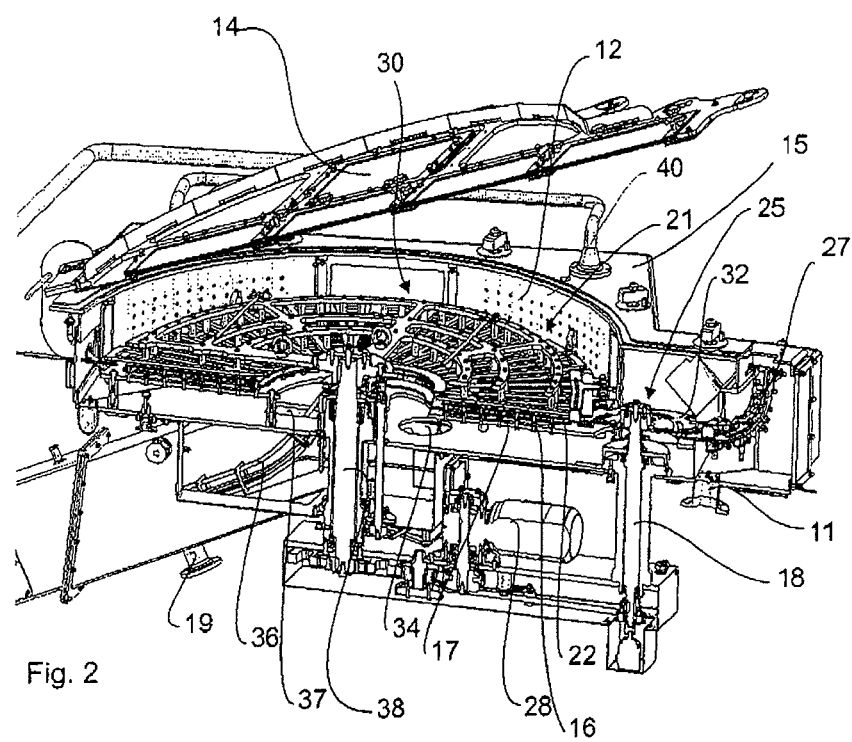
FIG. 2 shows a view in partial cross section of the arrangement of FIG. 1.

FIG. 2 shows a view in partial cross section of the arrangement 20 of FIG. 1. It can be seen that the feed device 25 comprises a closure feed chute 27 which delivers the container closures to an inlet star wheel 32. This feeding of the closures may take place in an air-assisted manner. This inlet star wheel 32 transports the closures horizontally to a spiral track which is denoted in its entirety by 30 and which forms the transport path 4. In the region of this spiral track 30, a displacement device 21 in the form of a rotor takes over the movement and guidance of the closures. Here, a driven shaft is provided which rotates the displacement device, the latter being denoted in its entirety by 21. Provided on this displacement device are displacement bodies (explained in detail below) which displace the container closures. The housing 2 has a circumferential wall 40 in which a large number of supply openings 12 are arranged, via which the gas can be guided into the housing 2.

The inlet star wheel 32 likewise has a drive shaft 18 which drives this inlet star wheel 32 in rotation. In this embodiment, a drive device, such as a motor 28, drives both the shaft 38 and also the shaft 18 in synchronism. In the inlet region between the inlet star wheel 32 and the transport path 4, the container closures are guided on all sides.

Reference 17 denotes a support device in the form of a base plate. On the spiral track 30, the container closures rest on this preferably slotted base plate 17, and reference 16 denotes a guide device which is designed here as a spiral plate and which is arranged at a predefined distance, for example 5 mm, above the support device 17. Reference 22 denotes an individual displacement body, with a large number of such displacement bodies 22 being provided which extend in each case in the radial direction, as mentioned above. The guide device 16 thus defines the movement direction. The support or rotor 24 comprising the displacement bodies 22, which is arranged above the guide device, performs the actual displacement of the container closures. The container closures are in each case contacted on their base body for the displacement. This configuration has the advantage, that the closure moves horizontally here on a spiral track towards the centre of the machine; the closure is free at the top.

In this way, closures with differently designed dust caps or even without dust caps can be transported by the guide device 16, without the units having to be changed for this purpose. The only requirement in each case is an identical or at least similarly designed base body of the container closures.

These aforementioned transport units, that is to say both the inlet star wheel 32 and the displacement device 21, are accommodated inside the gas-tight housing 2. The shafts 18 and 38 are preferably equipped in each case with overload clutches. The motor 28 is preferably a centrally arranged geared motor.

Due to the evenly spaced arrangement of the supply openings 12, it is possible to distribute the gaseous medium evenly over the entire housing 2. Also provided in the housing are a large number of cleaning nozzles (not shown in detail) which serve for internal cleaning of the housing. The cleaning agent is drained via an opening 34 or a drainage pipe, which can be closed by flap valves. In total, the housing 2 has three such openings 34 and a (preferably rectangular) discharge opening 37 for the container closures.

Provided on the outer circumference of the housing are gas inlet chambers 15, via which the $H_2O_2$/air mixture is introduced into the treatment chamber, i.e. the housing 2. The gas speed itself and also eddies generated by the rotation of the displacement device 21 bring about an even distribution of the gas inside the chamber and also in the interior of the individual closures. This is advantageous for disinfection purposes. The inflowing gas can be aspirated via an aspiration tube 11 in the inlet region or in the feed device 25 and also via a tube 19 in the discharge device 35.

During operation, a slight overpressure prevails in the treatment chamber, i.e. in the region of the housing 2 in which the transport path 4 is arranged as a spiral track, and any escape of $H_2O_2$ into the environment is prevented by means of a vacuum in the inlet region, i.e. in the region of the housing in which the inlet star wheel 32 is arranged. A counterpressure in the region of the downstream filling device (not shown) prevents any penetration of $H_2O_2$ into the filling region. The required treatment temperature of the $H_2O_2$/air mixture is maintained by the temperature of the inflowing $H_2O_2$/air mixture and also by means of heating blankets (not shown)

which are arranged on the housing 2. Also preferably provided are pressure and temperature sensors which continuously monitor the operating states.

Figure 3:
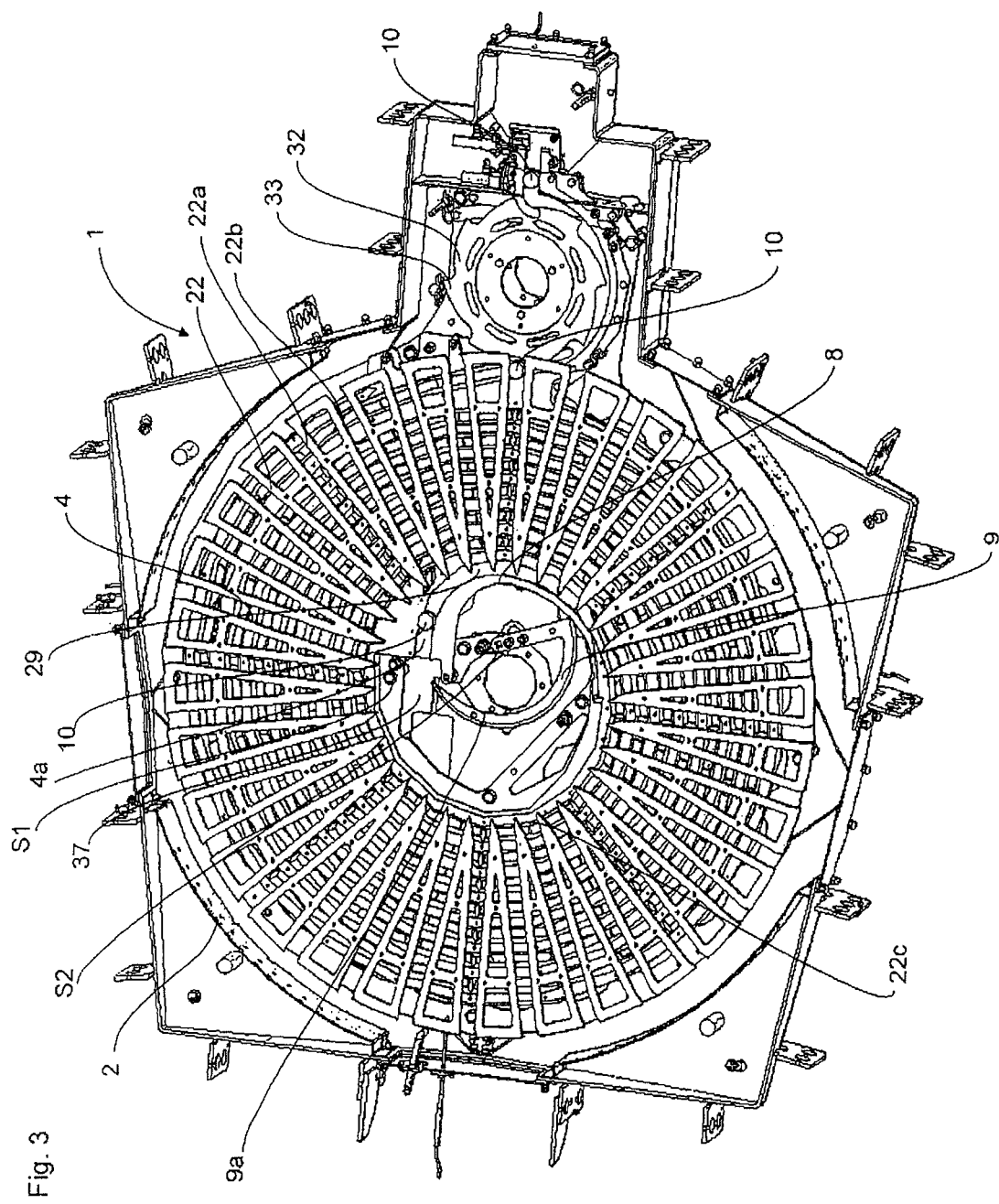
FIG. 3 shows a plan view of an apparatus according to the invention for disinfecting container closures.

FIG. 3 shows a plan view of an apparatus 1 according to the invention. The respective drive shafts for the inlet star wheel 32 and for the displacement device 21 are not shown here. The container closures 10 are fed to the inlet star wheel 32 via the abovementioned chute 27. The inlet star wheel 32 has a large number of sawtooth-shaped recesses 33 which serve for guiding the container closures 10. The inlet star wheel 32 delivers the container closures 10 to the displacement device 21, which is likewise shown in FIG. 3.

The displacement device 21 has, as mentioned above, a large number of displacement bodies 22 which in each case extend radially outwards. These displacement bodies 22 have the shape of a triangle which tapers radially inwards. In this way, the distances between individual guide edges 22a and 22b in each case remain substantially constant from the outside towards the inside, and thus in each case one container closure 10 can be received between the individual displacement bodies 22 with a defined amount of play. Furthermore, on the radially inner side, the displacement bodies have tapered portions or angled faces 22c which are inclined in such a way that the container closures are also urged inwards in the interior of the transport path 4.

Reference 4 thus denotes, in its entirety, the transport path which runs in a spiral manner from the outside towards the inside and along which the container closures 10 are guided. Provided at the end of this transport path 4 is a region 4a along which the container closures 10 are guided as far as the rectangular discharge opening 37, via which they are discharged from the housing 2. At the end of the transport path 4, the containers 10 will pass through an s-shaped transfer chute 36 (cf. FIG. 2). Via this chute, the container closures slide towards the closing device (not shown), optionally in an air-assisted manner.

Reference 8 denotes a first pivot lever which is arranged such that it can pivot with respect to a pivot point S1, and reference 9 denotes a second pivot lever which is arranged such that it can pivot with respect to a pivot point S2. These two pivot levers 8 and 9 serve for eliminating jams and can be operated manually from outside. The outer circumference of the first pivot lever 8 serves as a guide for the container closures 10. If a jam of the container closures occurs, this first pivot lever 8 can be tilted in the clockwise direction about the pivot axis S1 and thus frees the path radially inwards for the container closures.

If this does not yet cause all the container closures 10 to accumulate in the central region of the housing 2, a second pivot lever 9 can likewise be pivoted in the clockwise direction, this time about the pivot point S2, so that its tip enters the transport path 4. The inner wall 9a of this second pivot lever 9 then serves as a guide for the container closures 10, so that the container closures 10 are also in this way urged into the centre of the housing 2.

Figure 4:
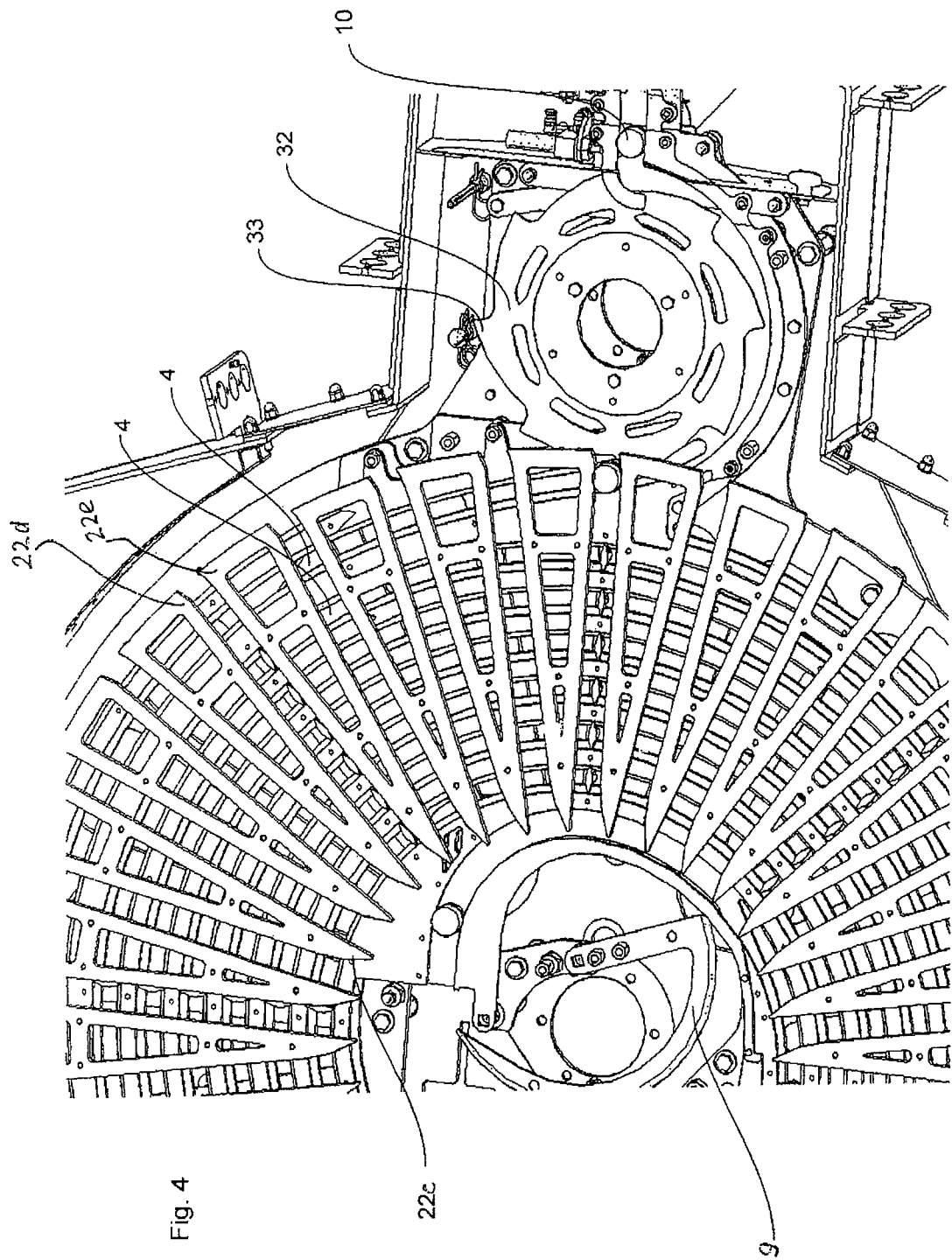
FIG. 4 shows an enlarged view of a sub-region of the view shown in FIG. 3.

FIG. 4 shows a more detailed view of the diagram from FIG. 3. It is again possible to see here the transport path 4, which extends in a spiral manner from the outside towards the inside. There can also be seen on the support device 17 a guide chute 29 for the container closures 10. It is also possible to see once again the tips 22c of the displacement bodies 22, which in the inner region likewise urge the container closures radially inwards, that is to say in the direction of the first pivot lever 8. At their radially outer region, the displacement bodies 22 have a portion 22d which is curved in the direction of rotation of the displacement bodies 22, and also a correspondingly curved region 22e on the next displacement body in each case.

All of the features disclosed in the application documents are claimed as essential to the invention in so far as they are novel individually or in combination with respect to the prior art.

The invention claimed is:

1. Apparatus for disinfecting container closures, comprising:
a housing;
a spiral transport path which is arranged inside the housing and along which the closures are transported, wherein the spiral transport path has at least partially a spiral configuration and winds around a fixed center point at an increasing or decreasing distance from the center point;
a supply device for supplying to the housing a gaseous medium for disinfecting the container closures; and
a displacement device which can move with respect to the housing and which transports the container closures along the spiral transport path, wherein the container closures are transported along the spiral configuration portion of the spiral transport path from an outside position towards the inside.

2. Apparatus according to claim 1, comprising a support device, along which the closures are displaced, wherein the support device is a base on which the closures rest and along which they are moved.

3. Apparatus according to claim 2, wherein the displacement device comprises a large number of displacement bodies which displace the closures along the support devices and which are arranged such that they can rotate around a common axis.

4. Apparatus according to claim 3, wherein the displacement bodies have an outer section which is curved in the movement direction.

5. Apparatus according to claim 4, wherein the displacement bodies also have a region which is inclined with respect to the radial direction of the displacement bodies.

6. Apparatus according to claim 3, wherein the displacement bodies have, on the radially inner side, tapered portions or angled faces, which are inclined in such a way, that the container closures are also urged inwards in the interior of the transport path.

7. Apparatus according to claim 3, wherein displacement bodies have the shape of a triangle which tapers radially inwards.

8. Apparatus according to claim 3 applied to a disinfecting operation.

9. Apparatus according to claim 1, wherein the housing also has an inlet region, via which the container closures are fed in, and an outlet region, via which the container closures are discharged.

10. Apparatus according to claim 9, wherein an aspirating device for the gaseous medium is provided at least in the outlet region or/and in the inlet region.

11. Apparatus according to claim 1, comprising a feed device, which is arranged at the outer circumference of the transport path.

12. Apparatus according to claim 11, wherein the feed device comprises a transport wheel which feeds the closures individually to the transport path.

13. Apparatus according to claim 11 or 12, wherein the feed device is an inlet star wheel.

14. Apparatus according to claim 11, wherein the housing is a gas-tight housing and the feed device and the displacement device are accommodated inside the gas-tight housing.

15. Apparatus according to claim 11, wherein the gaseous medium is at least temporarily at a higher pressure in the region of the housing in which the transport path is provided than in the region of the housing in which the feed device is provided.

16. Apparatus according to claim 1, wherein the transport path is adjoined by a transport chute with an S shaped profile, wherein via this transport chute, the container closures are conveyed out of the apparatus.

17. Apparatus according to claim 1, wherein the outlet of the housing is located in a cleanroom.

18. Apparatus according to claim 1, wherein the housing has a rectangular discharge opening for the container closures.

19. Apparatus according to claim 18, wherein provided at the end of the transport path a region is provided, along which the container closures are guided as far as the rectangular discharge opening via which they are discharged from the housing.

20. Apparatus for disinfecting container closures, comprising:
  a housing;
  a transport path which is arranged inside the housing and along which the closures are transported, wherein the transport path has at least partially a spiral configuration and winds around a fixed center point at an increasing or decreasing distance from the center point;
  a supply device for supplying to the housing a gaseous medium for disinfecting the container closures; and
  a displacement device which moves with respect to the housing and which transports the container closures along the spiral configuration of the transport path, wherein the container closures are transported along the spiral configuration of the transport path from an outside position towards the inside, wherein the transport path is constructed and arranged so that the container closures are transported from an outside position towards the inside along the spiral configuration of the transport path, and wherein the device comprises a feed device, which is arranged at an outer circumference of the transport path.

* * * * *